(12) United States Patent
Baughman

(10) Patent No.: US 7,998,145 B2
(45) Date of Patent: Aug. 16, 2011

(54) SELECTIVELY LOCKING DEVICE

(75) Inventor: Tyler Baughman, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1228 days.

(21) Appl. No.: 11/670,040

(22) Filed: Feb. 1, 2007

(65) Prior Publication Data
US 2007/0186596 A1   Aug. 16, 2007

Related U.S. Application Data

(63) Continuation of application No. 10/302,410, filed on Nov. 22, 2002, now abandoned.

(51) Int. Cl.
*A61F 2/84* (2006.01)
(52) U.S. Cl. .......................................................... 606/99
(58) Field of Classification Search .................... 606/99, 606/108, 194, 200
See application file for complete search history.

(56) References Cited

U.S. PATENT DOCUMENTS

| | | | |
|---|---|---|---|
| 3,472,230 A | 10/1969 | Fogarty | |
| 3,952,747 A | 4/1976 | Kimmell, Jr. | |
| 3,996,938 A | 12/1976 | Clark, III | |
| 4,425,908 A | 1/1984 | Simon | |
| 4,613,329 A | 9/1986 | Bodicky | |
| 4,643,184 A | 2/1987 | Mobin-Uddin | |
| 4,662,885 A | 5/1987 | DiPisa, Jr. | |
| 4,706,671 A | 11/1987 | Weinrib | |
| 4,723,549 A | 2/1988 | Wholey et al. | |
| 4,790,812 A | 12/1988 | Hawkins, Jr. et al. | |
| 4,790,813 A | 12/1988 | Kensey | |
| 4,794,928 A | 1/1989 | Kletschka | |
| 4,857,045 A | 8/1989 | Rydell | |
| 4,873,978 A | 10/1989 | Ginsburg | |
| 4,886,061 A | 12/1989 | Fischell et al. | |
| 4,969,891 A | 11/1990 | Gewertz | |
| 5,011,488 A | 4/1991 | Ginsburg | |
| 5,071,407 A | 12/1991 | Termin et al. | |
| 5,133,733 A | 7/1992 | Rasmussen et al. | |
| 5,160,342 A | 11/1992 | Reger et al. | |
| 5,192,286 A | 3/1993 | Phan et al. | |
| 5,324,304 A | 6/1994 | Rasmussen | |
| 5,329,942 A | 7/1994 | Gunther et al. | |
| 5,370,657 A | 12/1994 | Irie | |
| 5,415,630 A | 5/1995 | Gory et al. | |

(Continued)

FOREIGN PATENT DOCUMENTS
WO         96/01591 A1     1/1996

*Primary Examiner* — Eduardo C Robert
*Assistant Examiner* — David Comstock
(74) *Attorney, Agent, or Firm* — Seager, Tufte & Wickhem LLC

(57) ABSTRACT

A locking element comprising a frame defining a central lumen through which a portion of the elongate member fits; one or more levers extending in the second direction from the frame able to be moved between a locking position and a releasing position; and one or more tabs extending in the first direction from the frame able to be moved by the one or more levers between a locked position and a released position; wherein when the locking element is disposed on an enabling elongate member in a second direction from a second cross section, the one or more tabs prevent the locking element from moving in a first direction beyond a first cross section when disposed in the locked position and do not prevent the locking element from moving in the first direction when disposed in the released position.

27 Claims, 9 Drawing Sheets

U.S. PATENT DOCUMENTS

| | | | |
|---|---|---|---|
| 5,419,774 A | 5/1995 | Willard et al. |
| 5,462,529 A | 10/1995 | Simpson et al. |
| 5,536,242 A | 7/1996 | Willard et al. |
| 5,549,626 A | 8/1996 | Miller et al. |
| 5,662,671 A | 9/1997 | Barbut et al. |
| 5,669,933 A | 9/1997 | Simon et al. |
| 5,769,816 A | 6/1998 | Barbut et al. |
| 5,779,716 A | 7/1998 | Cano et al. |
| 5,800,402 A | 9/1998 | Bierman |
| 5,800,457 A | 9/1998 | Gelbfish |
| 5,800,525 A | 9/1998 | Bachinski et al. |
| 5,807,398 A | 9/1998 | Shaknovich |
| 5,814,064 A | 9/1998 | Daniel et al. |
| 5,827,324 A | 10/1998 | Cassell et al. |
| 5,833,650 A | 11/1998 | Imran |
| 5,848,964 A | 12/1998 | Samuels |
| 5,911,734 A | 6/1999 | Tsugita et al. |
| 5,947,995 A | 9/1999 | Samuels |
| 6,001,118 A | 12/1999 | Daniel et al. |
| 6,010,531 A | 1/2000 | Donlon et al. |
| 6,066,149 A | 5/2000 | Samson et al. |
| 6,066,158 A | 5/2000 | Engelson et al. |
| 6,129,739 A | 10/2000 | Khosravi |
| 6,142,987 A | 11/2000 | Tsugita |
| 6,152,946 A | 11/2000 | Broome et al. |
| 6,152,947 A | 11/2000 | Ambrisco et al. |
| 6,168,579 B1 | 1/2001 | Tsugita |
| 6,171,327 B1 | 1/2001 | Daniel et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,221,006 B1 | 4/2001 | Dubrul et al. |
| 6,277,138 B1 | 8/2001 | Levinson et al. |
| 6,277,139 B1 | 8/2001 | Levinson et al. |
| 6,290,710 B1 | 9/2001 | Cryer et al. |
| 6,312,407 B1 | 11/2001 | Zadno-Azizi et al. |
| 6,336,934 B1 | 1/2002 | Gilson et al. |
| 6,371,971 B1 | 4/2002 | Tsugita et al. |
| 6,425,909 B1 | 7/2002 | Dieck et al. |
| 6,527,746 B1 | 3/2003 | Oslund et al. |
| 6,530,939 B1 | 3/2003 | Hopkins et al. |
| 6,537,294 B1 | 3/2003 | Boyle et al. |
| 6,537,295 B2 | 3/2003 | Petersen |
| 6,537,296 B2 | 3/2003 | Levinson et al. |
| 6,544,279 B1 | 4/2003 | Hopkins et al. |
| 6,589,263 B1 | 7/2003 | Hopkins et al. |
| 6,605,102 B1 | 8/2003 | Mazzocchi et al. |
| 6,616,680 B1 | 9/2003 | Thielen |
| 6,645,224 B2 | 11/2003 | Gilson et al. |
| 6,740,061 B1 | 5/2004 | Oslund et al. |
| 6,743,247 B1 | 6/2004 | Levinson et al. |
| 6,773,448 B2 | 8/2004 | Kusleika et al. |
| 6,843,798 B2 | 1/2005 | Kusleika et al. |
| 6,902,572 B2 | 6/2005 | Beulke et al. |
| 6,936,059 B2 | 8/2005 | Belef |
| 6,939,361 B1 | 9/2005 | Kleshinski |
| 6,962,598 B2 | 11/2005 | Linder et al. |
| 6,969,396 B2 | 11/2005 | Krolik et al. |
| 7,014,647 B2 | 3/2006 | Brady et al. |
| 7,118,539 B2 | 10/2006 | Vrba et al. |
| 2001/0023333 A1 | 9/2001 | Wise et al. |
| 2001/0041908 A1 | 11/2001 | Levinson et al. |
| 2002/0095174 A1 | 7/2002 | Tsugita et al. |
| 2002/0111648 A1 | 8/2002 | Kusleika et al. |
| 2002/0121472 A1 | 9/2002 | Garner et al. |
| 2002/0128678 A1 | 9/2002 | Petersen |
| 2002/0161395 A1 | 10/2002 | Douk et al. |
| 2002/0183782 A1 | 12/2002 | Tsugita et al. |
| 2003/0004539 A1 | 1/2003 | Linder et al. |
| 2003/0004540 A1 | 1/2003 | Linder et al. |
| 2003/0004541 A1 | 1/2003 | Linder et al. |
| 2003/0069523 A1 | 4/2003 | Williams et al. |
| 2003/0074019 A1 | 4/2003 | Gray et al. |
| 2003/0078614 A1 | 4/2003 | Salahieh et al. |
| 2003/0163064 A1 | 8/2003 | Vrba et al. |
| 2003/0176887 A1 | 9/2003 | Petersen |
| 2003/0181942 A1 | 9/2003 | Sutton et al. |
| 2003/0212433 A1 | 11/2003 | Ambrisco et al. |
| 2003/0212434 A1 | 11/2003 | Thielen |
| 2004/0088002 A1 | 5/2004 | Boyle et al. |
| 2004/0158276 A1 | 8/2004 | Barbut et al. |
| 2004/0158280 A1 | 8/2004 | Morris et al. |
| 2004/0193207 A1 | 9/2004 | Boismier |
| 2004/0193209 A1 | 9/2004 | Pavcnik et al. |
| 2004/0220612 A1 | 11/2004 | Swainston et al. |
| 2004/0249409 A1 | 12/2004 | Krolik et al. |
| 2004/0267301 A1 | 12/2004 | Boylan et al. |
| 2005/0010247 A1 | 1/2005 | Kusleika et al. |
| 2005/0027345 A1 | 2/2005 | Horan et al. |
| 2005/0090810 A1 | 4/2005 | Petersen |
| 2005/0101986 A1 | 5/2005 | Daniel et al. |
| 2005/0101987 A1 | 5/2005 | Salahieh |
| 2005/0131449 A1 | 6/2005 | Salahieh et al. |
| 2005/0166841 A1 | 8/2005 | Robida |
| 2006/0015139 A1 | 1/2006 | Tsugita et al. |
| 2006/0015141 A1 | 1/2006 | Linder et al. |
| 2006/0030876 A1 | 2/2006 | Peacock, III et al. |
| 2006/0089663 A1 | 4/2006 | Gilson et al. |
| 2006/0089665 A1 | 4/2006 | Eskuri et al. |
| 2006/0089666 A1 | 4/2006 | Linder et al. |
| 2006/0111689 A1 | 5/2006 | Rosenschein et al. |
| 2006/0136041 A1 | 6/2006 | Schmid et al. |
| 2006/0155320 A1 | 7/2006 | Bressler et al. |
| 2006/0155321 A1 | 7/2006 | Bressler et al. |
| 2006/0224176 A1 | 10/2006 | Fung et al. |
| 2007/0005102 A1 | 1/2007 | Keating et al. |
| 2007/0021775 A1 | 1/2007 | Vrba et al. |
| 2007/0032854 A1 | 2/2007 | Schmid et al. |

SELECTIVELY LOCKING DEVICE

This is a continuation of U.S. application Ser. No. 10/302,410, filed Nov. 22, 2002.

FIELD OF THE INVENTION

The present invention generally pertains to apparatus and methods for deploying and retrieving a medical device from an elongate member. More particularly, the present invention generally pertains to apparatus and methods useful for locking a medical device on an elongate member and subsequently releasing the medical device.

SUMMARY OF THE INVENTION

Embodiments of the invention pertain to a selectively locking element that may be attached to a medical device such as a filter or therapeutic deliver device and may be disposed on an elongate member such as a guidewire. The selectively locking element enables the medical device to be disposed on the elongate member such that it will stay on the elongate member past a transition region. The elongate member should be configured to enable the selectively locking element to lock. This may be done by providing a first region of the elongate member that has a distance to the central longitudinal axis that is less than the distance to the central longitudinal axis of a proximal region in a direction along the central longitudinal axis. A guidewire having a raised region on it would be an example of an elongate member that enables the selectively locking element. The selectively locking element may comprise one or more tabs and corresponding levers, where the tabs have a locked position and a released position and the levers have a corresponding locking position and releasing position. The tabs may be biased to the locked position. When the selectively locking element is moved in a first longitudinal direction over the first region, the tabs may move into the locked position, preventing moving of the selectively locking element back in the second longitudinal direction. A catheter or other object may be used to move the levers to the releasing position, thereby moving the tabs to the released position and allowing movement of the selectively locking element in the second direction. Various centering elements may be used. For example, centering arms may be attached to the levers, such that when the levers are moved to the releasing position, the centering arms position the selectively locking element centrally about the elongate member. A centering frame may extend from the selectively locking element in the second direction over a region of the guidewire in a second direction from the first region and thereby keep the locking element centered with respect to the elongate member. The elongate member may also include an anti-rotation features, which may be used to orient the selectively locking element remotely. These anti-rotation features may include one or more flat regions on the elongate member, or one or more longitudinal grooves or ridges. Radial or longitudinal radiopaque markings may be used. These embodiments, variations thereon, and other embodiments, together with advantages thereof, will be discussed at length below.

DETAILED DESCRIPTION OF THE INVENTION

The following detailed description should be read with reference to the drawings in which like elements in different drawings are number in like fashion. The drawings, which are not necessarily to scale, depict selected embodiments and are not intended to limit the scope of the invention. Those skilled in the art will recognize that many of the examples provided have suitable alternatives that may be utilized.

Figure 1:
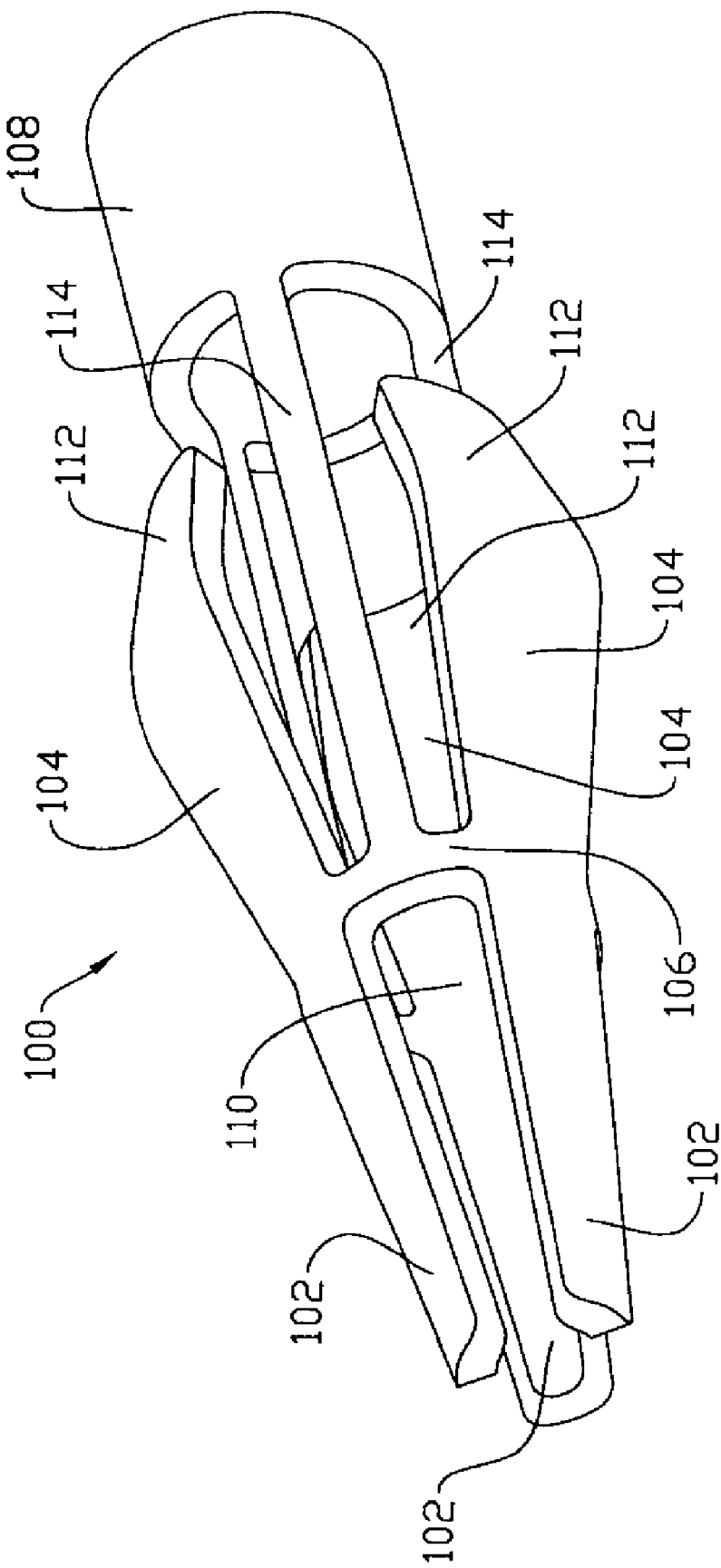
FIG. 1 is an orthographic view of an embodiment in accordance with the invention.

FIG. 1 is an orthographic view of a locking element 100 attached to a medical device 108 in accordance with the present invention. As will be readily appreciated from further description, medical device 108 may be any suitable medical device such as a filter or therapeutic delivery device. Locking element 100 includes tabs 102, which move between a locked position and a released position. In this figure, tabs 102 are shown in a locked position and in this embodiment, tabs 102 are biased to be in a locked position. Locking element 100 also includes levers 104, which move between a locking position and a released position. In this figure, levers 104 are shown in a locking position and in this embodiment, levers 104 are biased to be in a locking position. Tabs 102 and levers 104 are disposed on frame 106, through which a lumen 110 is disposed. The free ends of tabs 102 are in a first direction from the fixed ends of tabs 102. Likewise, the fixed ends of tabs 102 are in a second direction from the free ends of tabs 102. These reference directions will remain constant throughout the several embodiments described. Centering arms 112 may be attached to the second direction ends of levers 104. While medical device 108 is attached to locking element 100 through struts 114 extending in a second direction from frame 106, it may be readily appreciated that medical device 108 may be attached through other means such as to levers 104 or centering arms 112.

The number and configuration of tabs 102 and levers 104 is, of course, not limited to that depicted in FIG. 1. While three tabs 102 and three levers 104 are depicted, embodiments employing as few as one tab 102 or one lever 104 have been contemplated. Likewise, embodiments employing more tabs 102 or levers 104 have been contemplated and the number of tabs or levers used is limited only by the engineering considerations of the particular embodiment. Similarly, although tabs 102 and levers 104 are shown in FIG. 1 to be in longitudinal alignment, embodiments have been contemplated where tabs 102 and levers 104 are not in alignment. Alignment of tabs 102 and levers 104 is not essential to the invention. As an example, the tabs and levers will, of course, not be in longitudinal alignment when the number of tabs and levers differs. The tabs and levers will be connected to each other such that moving one or more levers from the locking to the releasing position moves one or more tabs from the locked to the released position. In the embodiment shown, tabs 102, levers 104 and frame 106 form a monolith unit. When levers 104 are moved from the locking position to the releasing position, a force is transmitted through the frame to tabs 102 to move the tabs to the released position. Other means of connecting the levers and the tabs are contemplated, however. One such means is connecting the levers to the rods using gears or hinges. Another means is making a lever and a tab monolithic and pivotably attaching it to the frame using a spring to provide bias towards the locking position.

Locking element 100 may include elements such as radiopaque bands or longitudinal strips to ease radial and longitudinal position of the device.

Figure 2:
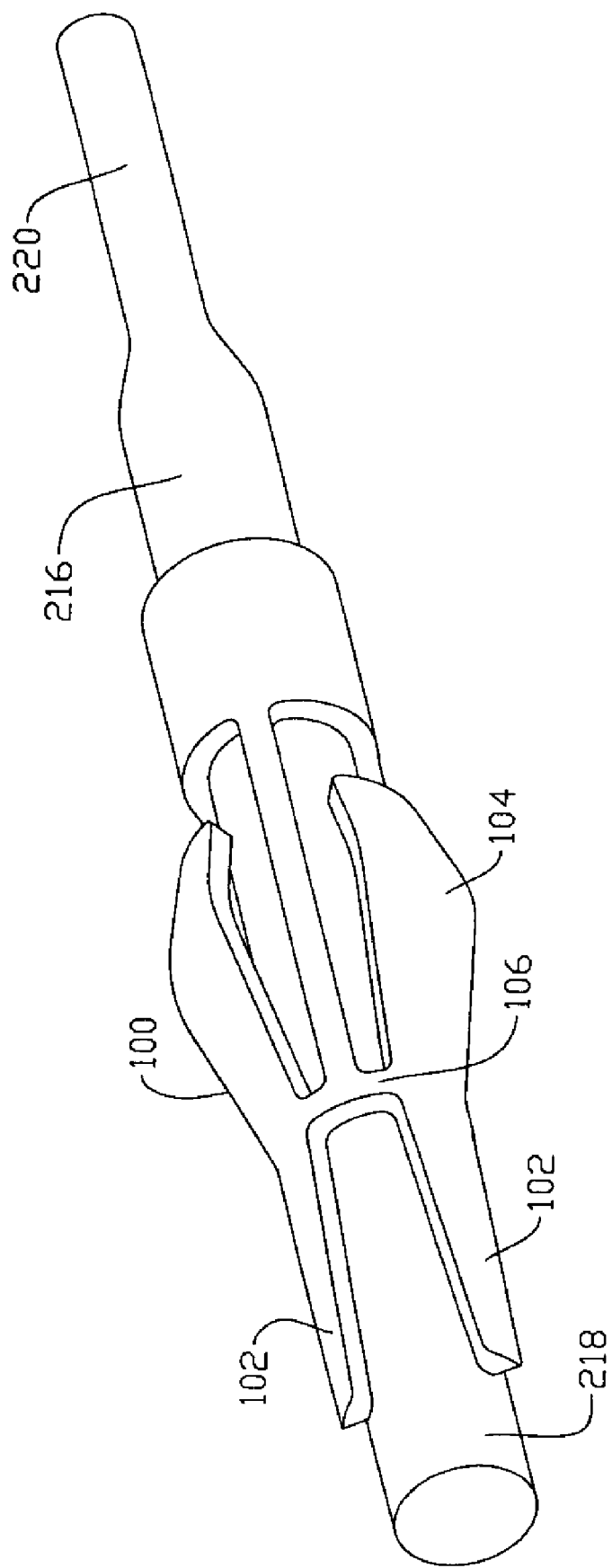
FIG. 2 is an orthographic view of the embodiment of FIG. 1 on an elongate member in accordance with the invention.

Turning to FIG. 2, one can see locking element 100 disposed on elongate member 216. Elongate member 216 has portion 218 in the first direction and portion 220 in the second direction. The transition between portion 218 and portion 220 is shown as a smooth transition with no sharp edges. The transition need not have this characteristic. Among other examples of suitable transitions, the transition may be a stepwise transition or be a simple frustoconical section, for example. Elongate member 216 is shown as having a circular cross section of uniform shape, but locking element 100 is not limited to being used with elongate members having this characteristic. Elongate member 216 may have any cross sectional shape where a portion of the elongate member in the first direction fits through frame 10. The cross sectional shape may, for example, be rectangular, triangular, or even irregular. Nor does a cross section at portion 220 need to be smaller than a cross section at portion 210. Portion 220 may have a longer perimeter or a larger cross sectional area than portion 218. What is important is that there is a surface region on portion 220 where the distance from the region to the central longitudinal axis of elongate member 216 is less than the distance from a surface region of portion 218 to the longitudinal axis. Thus, for example, an elongate member of generally uniform and circular cross section would suffice if there were a channel in the elongate member in portion 220. Likewise, an elongate member whose portion 220 was flattened and thereby had a reduced cross sectional thickness but an increased cross sectional width would also suffice. An elongate member of generally constant cross section that has a small region of increased or decreased cross sectional area may work as well.

Locking element 100 is disposed on portion 218 of elongate member 216. At this portion, tabs 102 are displaced outward by elongate member 216, allowing locking element move freely in the first and second directions.

Figure 3:
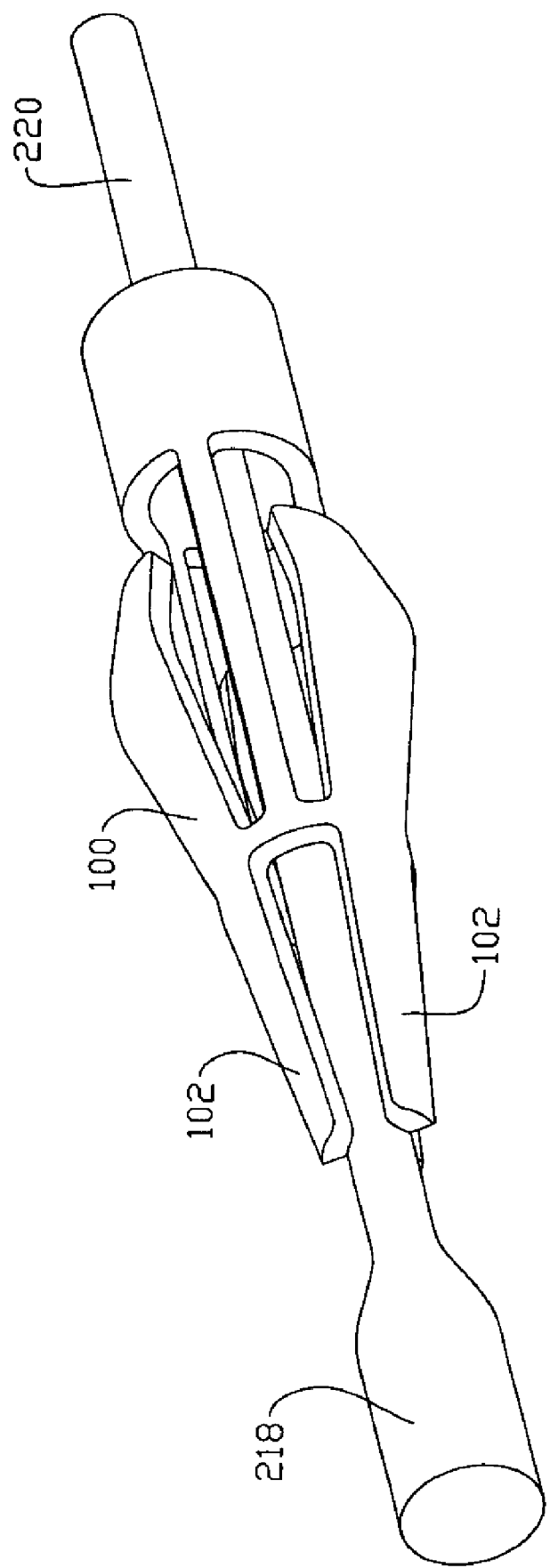
FIG. 3 is an orthographic view of the embodiment of FIG. 1 on a different portion of the elongate member of FIG. 2 in accordance with the invention.

Turning now to FIG. 3, locking element 100 is disposed on portion 220 of elongate member 216. Tabs 102 are in a locked position, preventing locking element 100 from being moved in the first direction onto portion 218.

Figure 4:
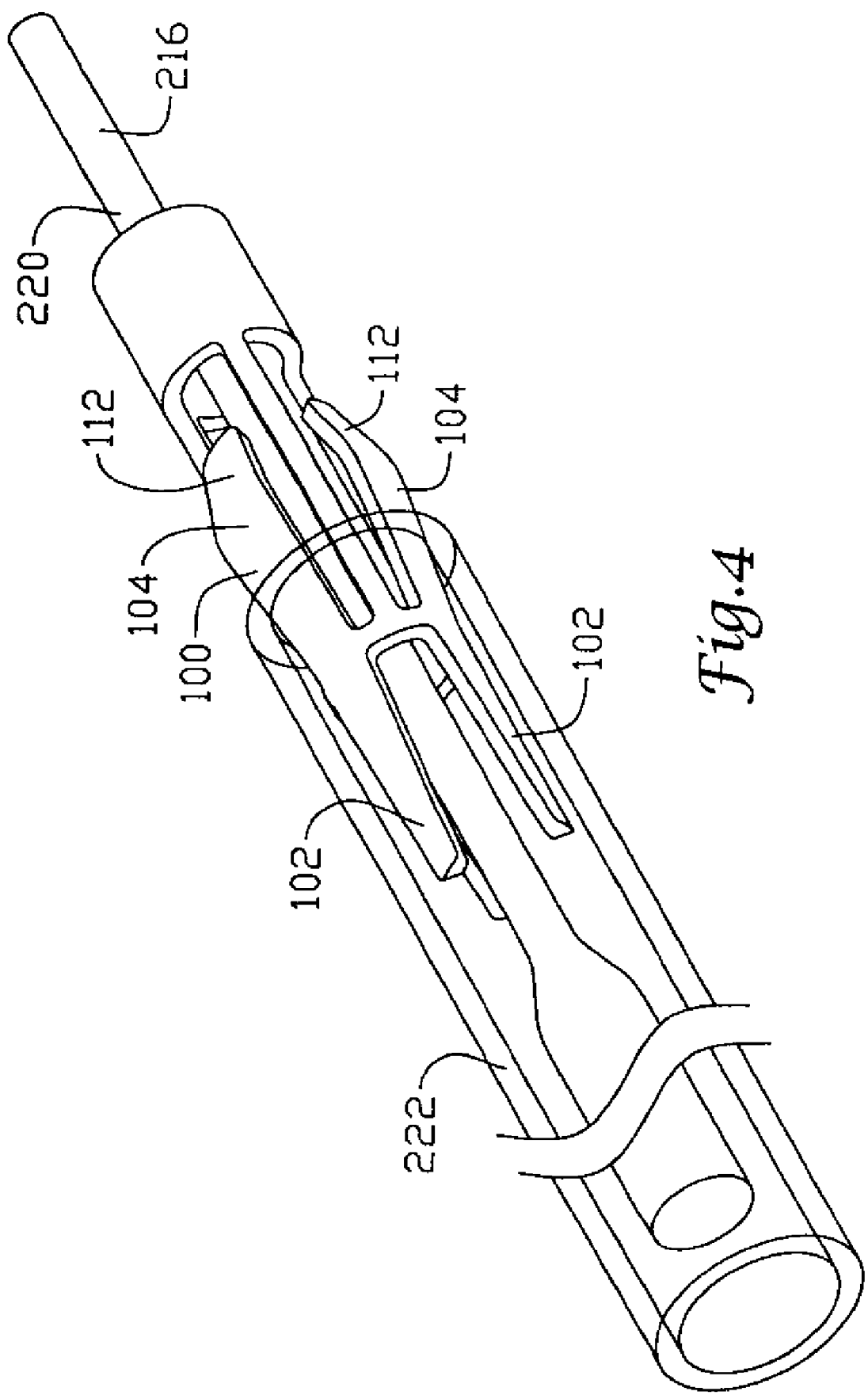
FIG. 4 is an orthographic view of the embodiment of FIG. 1 on the portion of the elongate member of FIG. 3 partially disposed in a catheter in accordance with the invention.

Turning now to FIG. 4, locking element 100 is disposed on portion 220 of elongate member 216. A catheter 222 is moved on locking element 100 in a second direction. Catheter 222 is sized to move levers 104 from a locking position to a releasing position. When levers 104 are in the releasing position, tabs 102 are moved to the released position and locking element 100 may be moved freely in the first or second direction. Of course, locking element 100 need not be operated using a catheter and other means of moving levers 104 are contemplated. For example, levers 104 could be operated manually or they could be wrapped in a band which shrinks after a period of time or a change of temperature. When levers 104 are in the releasing position, the free ends of centering arms 112 abut against elongate member 216 and generally center locking element 100 with respect to elongate member 216. This may ease the removal of locking element 100.

Figure 5:
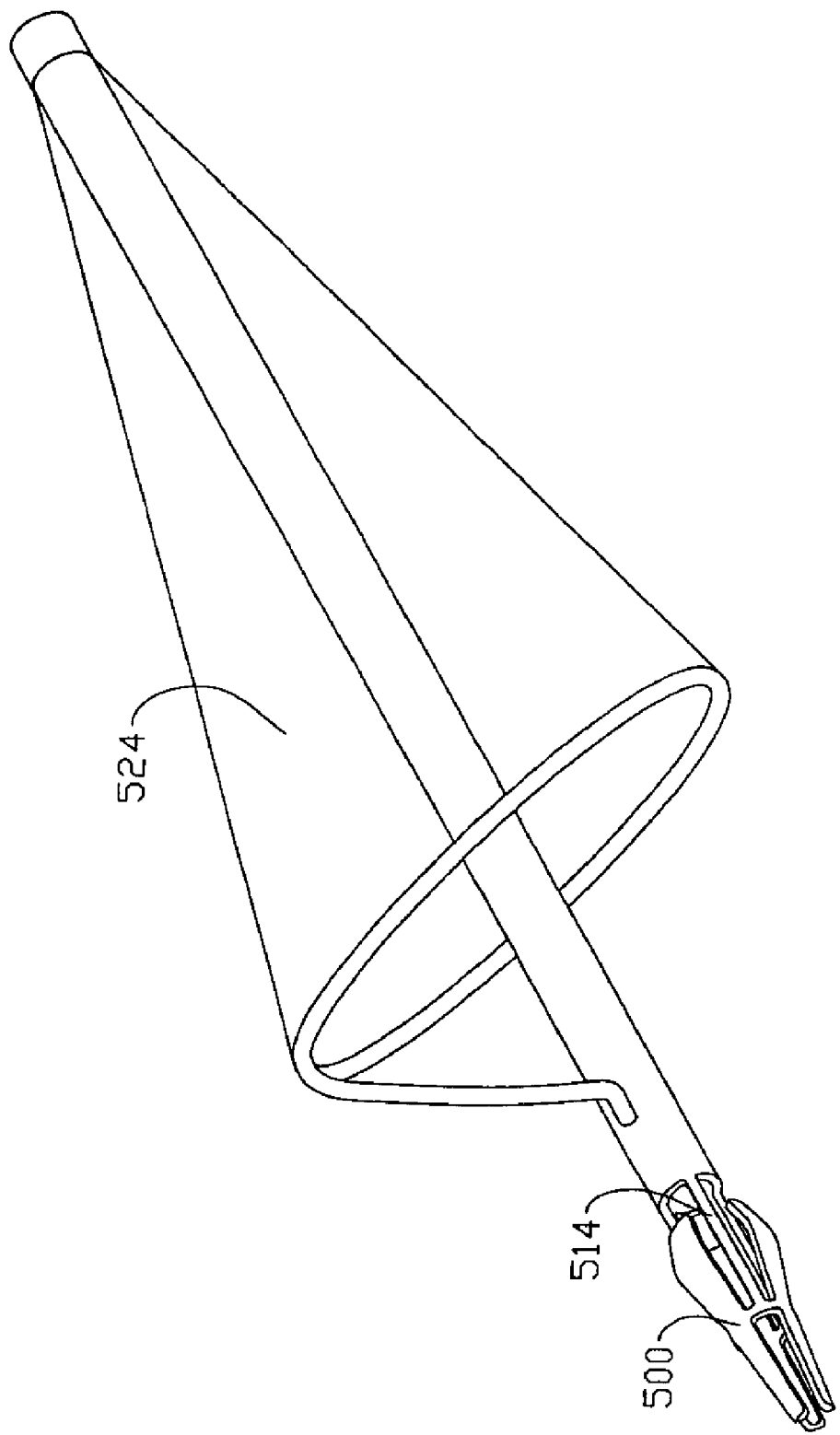
FIG. 5 is an orthographic view of the embodiment of FIG. 1 attached to a filter in accordance with the invention.

FIG. 5 is an orthographic view illustrating one use for a locking element 500, substantially similar to locking element 100. Locking element 500 is attached with struts 514 to filter 524, allowing the filter to be selectively locked on a guidewire, for example.

Figure 6:
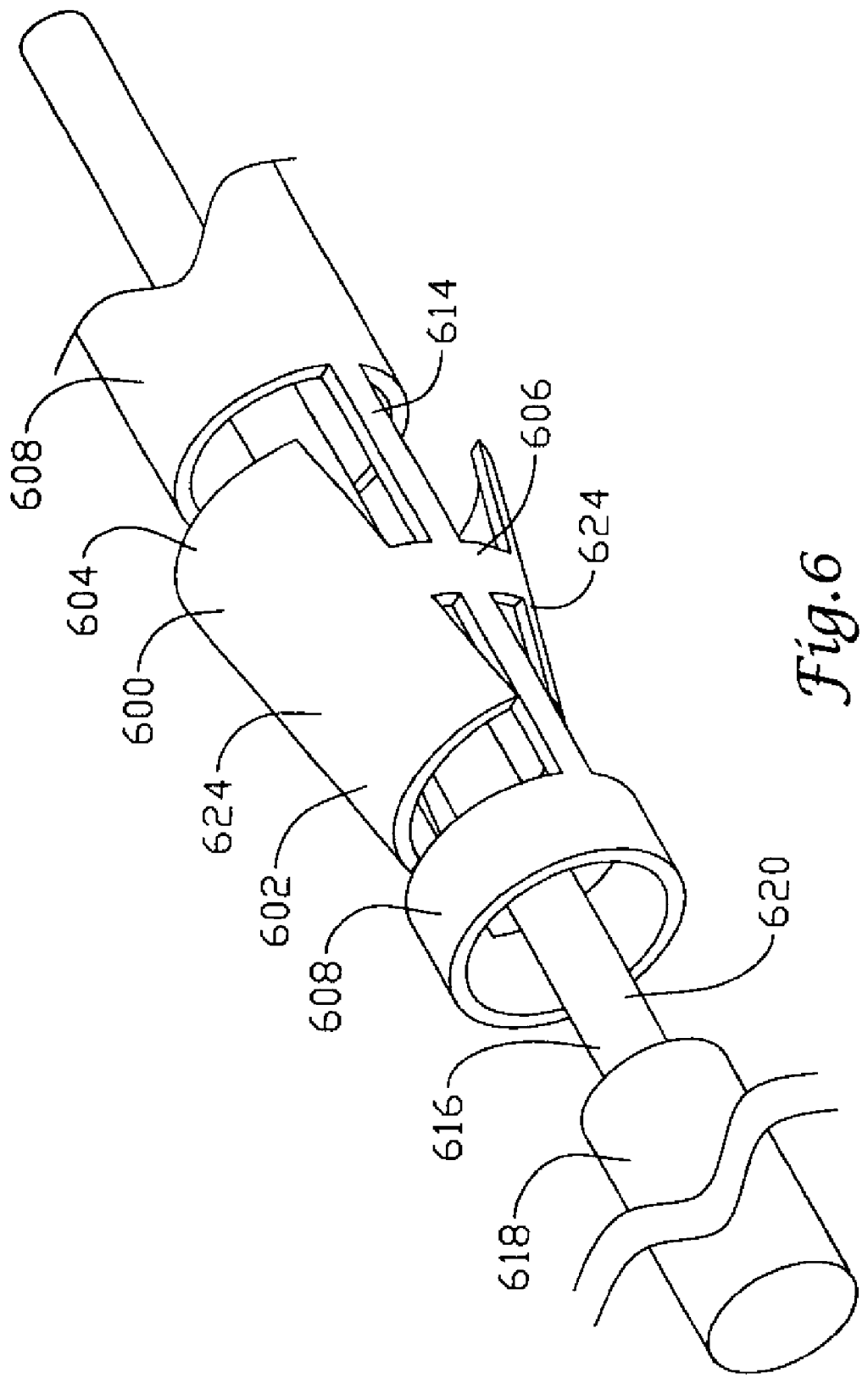
FIG. 6 is an orthographic view of an embodiment disposed on an elongate member in accordance with the invention.

FIG. 6 is an orthographic view illustrating a locking element 600 according to the invention. Locking element 600 has two limbs 624, each of which has a tab 602 and a lever 604. Levers 604 move between a locking and a releasing position and thereby move tabs 602 between a locked position and a released position. Tabs 602 may be biased to the locked position. Limbs 624 are connected to frame 606 from which may extend in a first and a second direction struts 614. Tubes 608 or medical devices may be attached to the struts. Locking element 600 may be disposed on elongate member 616 which has a portion in the first direction 618 and a portion in the second direction 620. Portion 620 has a surface region which is closer to the longitudinal axis than a surface region of portion 618. When locking element 600 is on portion 620 of elongate member 616 and tabs 602 are in the locked position, the locking element will be prevented from moving in the first direction onto portion 618. The tube 608 in the first direction from locking element 600 may have a centering function. When locking element 600 is on the portion 620 and tabs 602 are in the locked position, the tube may stay on portion 618 and thereby keep the locking element centered with respect to the elongate member.

Figure 7:
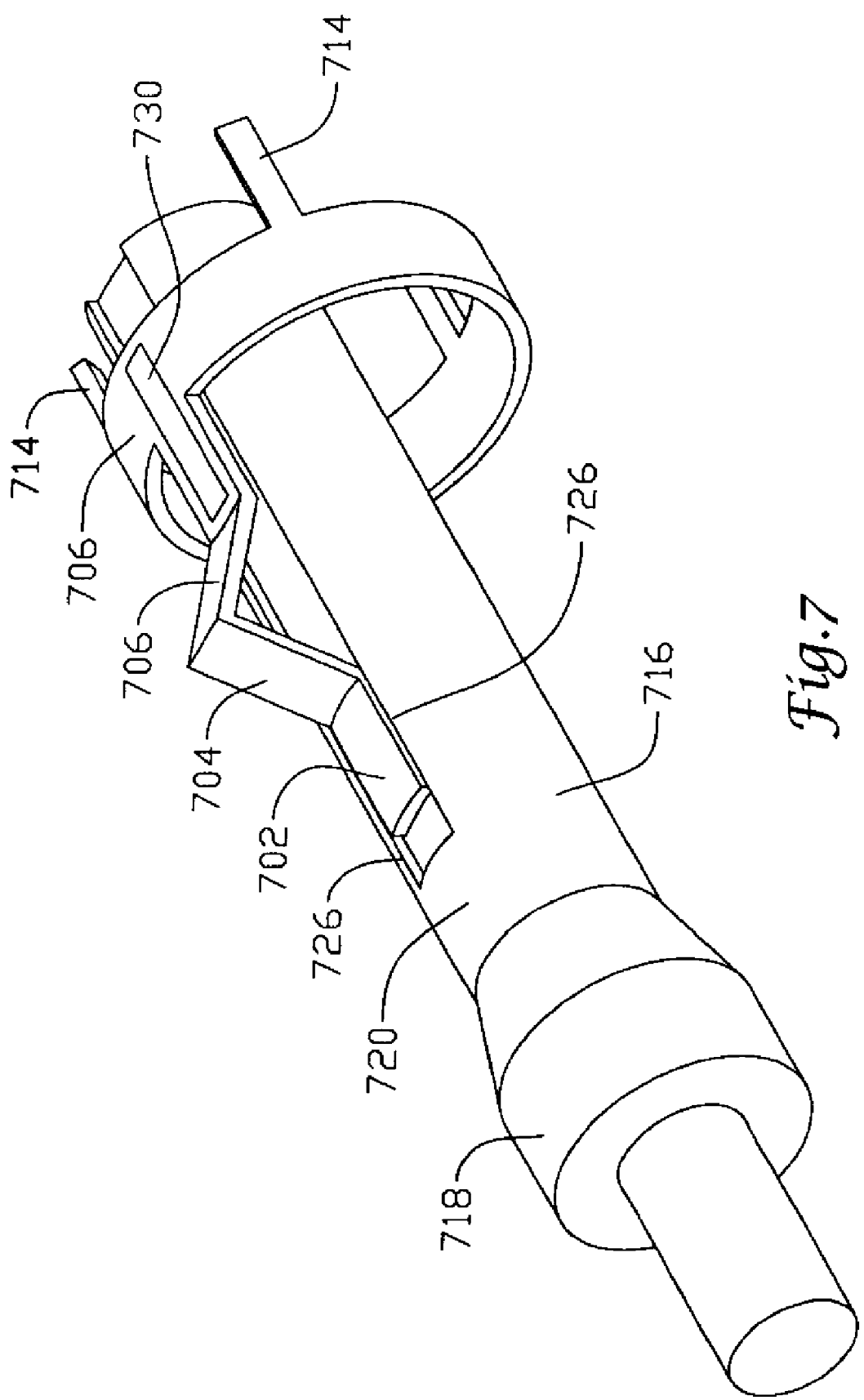
FIG. 7 is an orthographic view of an embodiment of the invention disposed on an elongate member in accordance with the invention.

FIG. 7 is an orthographic view illustrating a locking element 700 in accordance with the invention. Locking element 700 has a tab 702 attached to a lever 704. It is of course contemplated that the embodiment of FIG. 7 may have more than one set of tabs and levers. Lever 704 moves between a locking and a releasing position and thereby moves tab 702 between a locked position and a released position. Lever 704 is attached to frame 706. Extending in a second direction from frame 706 are struts 714, which may be connected to a medical device such as a filter or therapeutic deliver system. Locking element 700 is disposed on an elongate member 716. Elongate member has portion 718 and portion 720. Portion 720 contains a surface region where the distance from that surface region to a central longitudinal axis is less than the distance from a surface region of portion 718 to the central longitudinal axis. Portion 720 also has ridges 726 disposed on either side of this surface region. Tab 702 is adapted to fit within these ridges when it is in the locked position, thereby preventing rotation of the locking element with respect to the elongate member. This feature may be useful to orient the locking member and attached medical device remotely. Locking element 700 also includes a longitudinal radiopaque stripe 730. This radiopaque stripe may be used to determine the position of the locking element.

Figure 8:
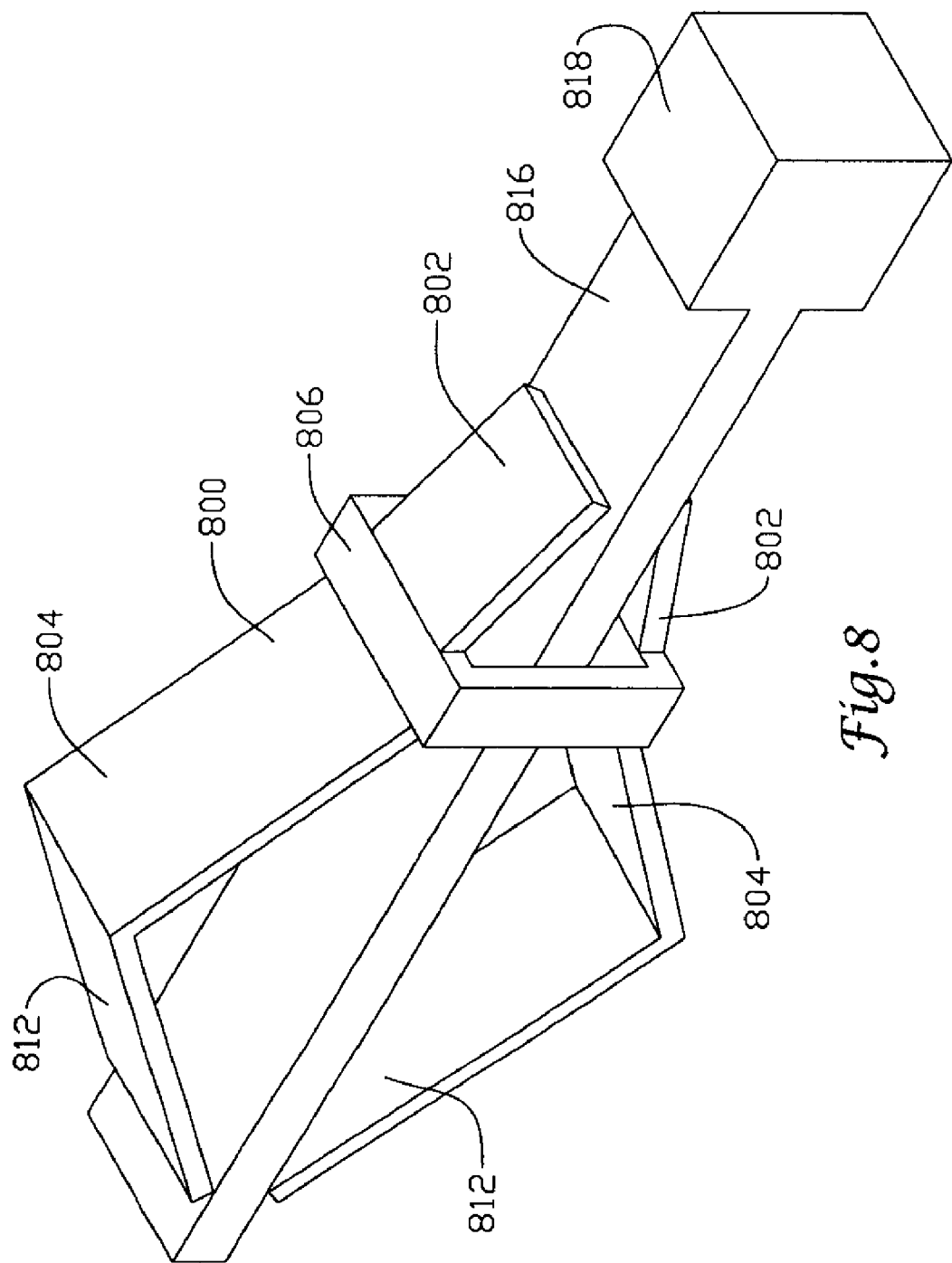
FIG. 8 is an orthographic view of an embodiment of the invention disposed on an elongate member in accordance with the invention.

FIG. 8 is an orthographic view illustrating a locking element 800 disposed on an elongate member 816 in accordance with the invention. Locking element 800 includes tabs 802, which may move between a locked position and a released position, and levers 804, which may move between a locking position and a releasing position. Tabs 802 and levers 804 are attached to a frame 806. Struts may extend in both directions from this frame, attached to medical or other devices. Centering elements 812 may be attached to the levers 804. When levers 804 are moved to the releasing position, tabs 802 are moved to the released position, thereby allowing locking device 800 to move over portion 818 of elongate member 816.

Figure 9:
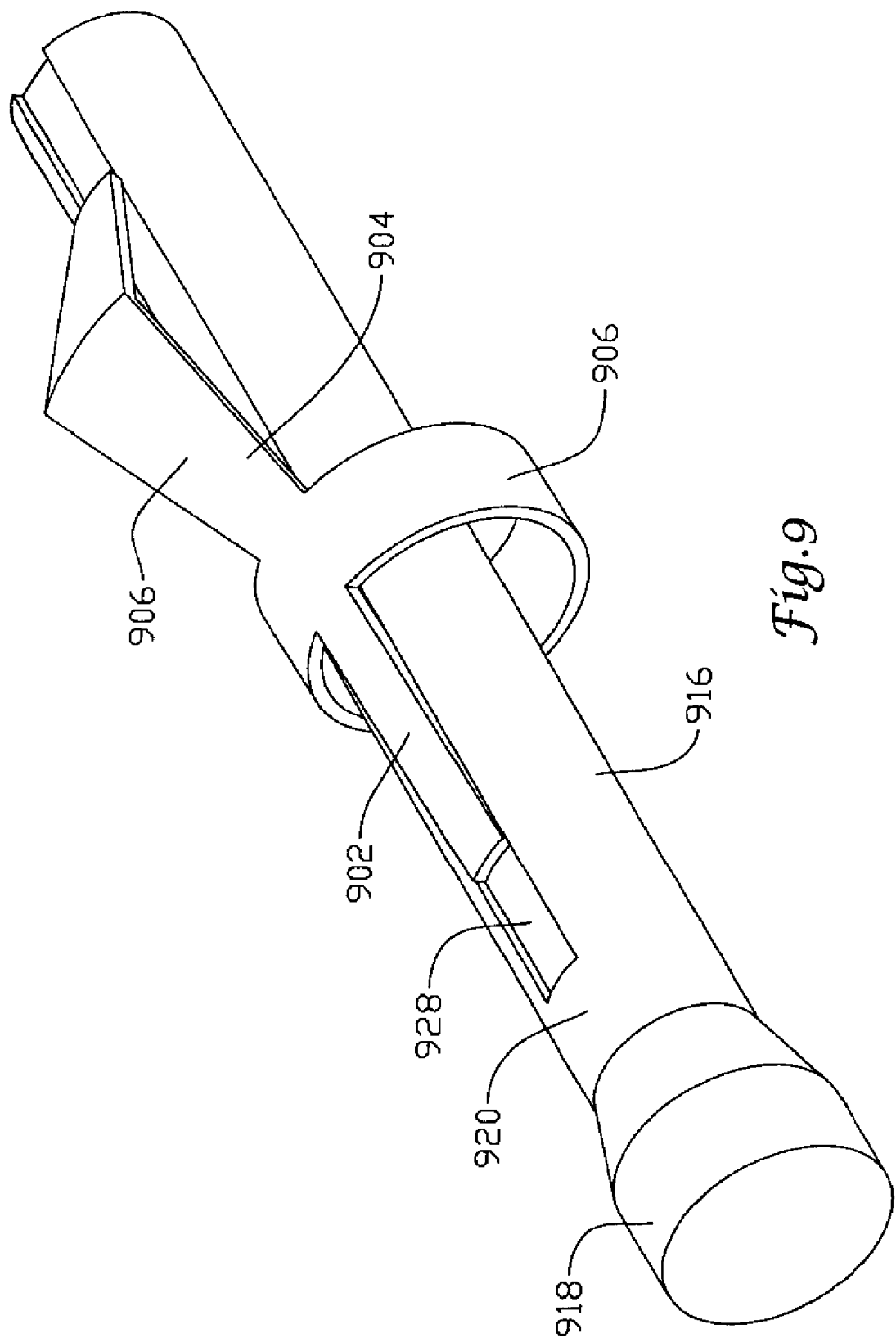
FIG. 9 is an orthographic view of an embodiment of the invention disposed on an elongate member in accordance with the invention.

FIG. 9 is an orthographic view illustrating a locking element 900 disposed on an elongate member 916 in accordance with the invention. Locking element 900 has a tab 902 attached to a lever 904. It is of course contemplated that the embodiment of FIG. 9 may have more than one set of tabs and levers. Lever 904 moves between a locking and a releasing position and thereby moves tab 902 between a locked position and a released position. Tab 902 and lever 904 are attached to a frame 906. Struts may extend in a second direction from frame 906, which may be connected to a medical device such as a filter or therapeutic deliver system. Locking element 900 is disposed on an elongate member 916. Elongate member has portion 918 and portion 920. Portion 920 contains a surface region where the distance from that surface region to a central longitudinal axis is less than the distance from a surface region of portion 918 to the central longitudinal axis. Portion 920 also has groove 928 disposed on portion 920. Tab 902 is adapted to fit in groove 928 when it is in the locked position, thereby preventing rotation of the locking element with respect to the elongate member. This feature may be useful to orient the locking member and attached medical device remotely.

In use, the locking element may be attached to a filter, therapeutic delivery device, or other medical device. The locking element may be slid in a distal direction over an elongate member. The elongate member will have a second portion in the second direction with a surface region that is closer to the central longitudinal axis of the elongate member than a surface region of a first portion of the elongate member. When the locking element is over the second portion, one or more tabs will move into the locked position, preventing movement in the first direction. To then allow the locking device to move in the first direction, the levers may be moved from the locking position to the releasing position thereby moving the tabs from the locked position to the released position. When the tabs are in the released position, the locking element may then be moved in the first direction.

As an illustrative example, suppose the selectively locking filter apparatus of FIG. 5 is put on a guidewire having a stepwise-reduced diameter, where the smaller diameter is distal the larger diameter, inserted percutaneously into a patient. The filter apparatus may be put into a catheter to reduce the diameter of the filter and advanced distally into the patient. When the filter apparatus is on the larger diameter portion of the guidewire, the tabs will be forced to a released position by the guidewire. When the filter apparatus passes the stepwise transition, the tabs will fall into the locked position and the catheter may be withdrawn. A catheter may then be introduced over the filter apparatus again, moving the levers to the releasing position and allowing the filter to be moved proximally off the guidewire.

The locking element may be made from any number of biocompatible materials. If the locking element is unitary, a combination of flexibility where the material bends at the frame and rigidity in the tabs and levers may be desirable. Merely as examples and not as an exhaustive list, such material may include metals such as stainless steel or Nitinol or may include plastics like nylon or polyvinylchloride. The material may be formed into the locking element or parts of the locking element by laser cutting, molding, welding, brazing or other process well known in the art.

It will be understood that this disclosure, in many respects, is only illustrative. Changes may be made in details, particularly in matters of shape, size, material, and arrangement of parts without exceeding the scope of the invention. Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A locking element for locking a medical device to an elongate member having a central longitudinal axis and a first cross section having a first perimeter and a second cross section having a second perimeter where a portion of the second perimeter is closer to the central longitudinal axis than a portion of the first perimeter, the locking element comprising:
   a frame defining a central lumen through which a portion of the elongate member fits;
   one or more levers extending in a second direction from the frame able to be moved between a locking position and a releasing position; and
   one or more tabs extending in a first direction from the frame able to be moved by the one or more levers between a locked position and a released position;
   wherein when the locking element is disposed on the elongate member in the second direction from the first cross section, the one or more tabs prevent the locking element from moving in the first direction onto the first cross section when disposed in the locked position and do not prevent the locking element from moving in the first direction onto the first cross section when disposed in the released position; and
   wherein when the locking element is disposed on the elongate member in the second direction from the first cross section, the levers are closer to the elongate member in the releasing position than in the locking position and the tabs are closer to the elongate member in the locked position than in the released position;
   wherein the locking element is monolithic.

2. The element of claim 1, wherein when the one or more levers is in the second direction from the first cross section, there is a gap between the one or more levers and a portion of the elongate member in the second cross section.

3. The element of claim 2, wherein the gap between the one or more levers and the elongate member increases in the second direction when the one or more levers are in the locked position.

4. The element of claim 1, wherein when the tabs are in the locked position, a portion of the one or more tabs cannot fit outside the first perimeter.

5. The element of claim 1, wherein moving the levers from the locking position to the releasing position causes the tabs to be moved from the locked position to the released position.

6. The element of claim 1, wherein the one or more levers and the one or more tabs are equal in number.

7. The element of claim 6, wherein each of the one or more tabs extend from the frame at a position opposite one of the tabs.

8. The element of claim 1, wherein the locking element further comprises struts to connect the locking element to a medical device.

9. The element of claim 8, wherein the struts are attached to the frame.

10. The element of claim 8, wherein the struts extend in the second direction from the locking element.

11. The element of claim 10, wherein the struts are attached to the levers.

12. The element of claim 1, wherein the locking element comprises a flexible material.

13. The element of claim 12, wherein the locking element comprises a super-elastic material.

14. The element of claim 13, wherein the locking element comprises a nickel-titanium alloy.

15. The element of claim 1, wherein the one or more levers and the one or more tabs are uniformly distributed around the frame.

16. The element of claim 1, wherein the one or more tabs comprise two opposing tabs and the one or more levers comprise two opposing levers.

17. The element of claim 1, wherein the one or more tabs comprise three equally spaced tabs and the one or more levers comprise three equally spaced levers.

18. The element of claim 1, wherein the one or more levers can be actuated by an object moving in the second direction.

19. The element of claim 1, wherein the one or more tabs are biased to the locked position.

20. The element of claim 1, wherein the one or more levers are biased to the locking position.

21. The element of claim 1, wherein the medical device is a filter.

22. The element of claim 1, wherein the element further comprises one or more radiopaque bands.

23. The element of claim 1, wherein the element further comprises one or more radiopaque longitudinal stripes.

24. The element of claim 1, wherein the one or more levers comprise two or more levers, further comprising:
   two or more centering arms attached to the two or more levers such that when the levers are moved to the releasing position, the two or more centering arms position the elongate member centrally with respect to the locking element.

25. A process for releasably locking a medical device on an elongate member, comprising:
   providing an elongate member having a central longitudinal axis and a first cross section having a first perimeter and a second cross section having a second perimeter where a portion of the second perimeter is closer to the central longitudinal axis than a portion of the first perimeter;
   providing a monolithic locking element on the first cross section, the locking element having a frame defining a lumen through which a portion of the elongate member may fit, one or more levers extending from the frame in a second direction able to be actuated between a locking position and a releasing position, and one or more tabs extending in a first direction from the frame able to be actuated by the one or more levers between a locked position and a released position, wherein when the locking element is disposed on the elongate member in the second direction from the first cross section, the levers are closer to the elongate member in the releasing position than in the locking position and the tabs are closer to the elongate member in the locked position than in the released position; and
   advancing the locking element on the elongate member in the second direction beyond the first cross section.

26. The process of claim 25, wherein when the locking element is advanced in the second direction beyond the first cross section, the one or more tabs move to the locked position.

27. The process of claim 25, further comprising the steps of:
   actuating the one or more levers to the releasing position; and
   advancing the locking element in the first direction beyond the first cross section.

* * * * *